United States Patent
Neher et al.

(10) Patent No.: US 7,304,733 B2
(45) Date of Patent: Dec. 4, 2007

(54) METHOD AND DEVICE FOR CONDUCTING THE SPECTRAL DIFFERENTIATING, IMAGING MEASUREMENT OF FLUORESCENT LIGHT

(75) Inventors: Erwin Neher, Bovenden (DE); Richard Neher, Bovenden (DE)

(73) Assignee: Max-Planck-Gesellschaft, Munich (DE)

( * ) Notice: Subject to any disclaimer, the term of this patent is extended or adjusted under 35 U.S.C. 154(b) by 382 days.

(21) Appl. No.: 10/515,673

(22) PCT Filed: May 15, 2003

(86) PCT No.: PCT/EP03/05094

§ 371 (c)(1),
(2), (4) Date: Nov. 22, 2004

(87) PCT Pub. No.: WO03/098174

PCT Pub. Date: Nov. 27, 2003

(65) Prior Publication Data

US 2005/0243313 A1 Nov. 3, 2005

(30) Foreign Application Priority Data

May 21, 2002 (DE) ................................ 102 22 359

(51) Int. Cl.
| | |
|---|---|
| *G01J 3/30* | (2006.01) |
| *G01J 1/58* | (2006.01) |
| *G01N 21/25* | (2006.01) |
| *F21V 9/16* | (2006.01) |
| *G01T 1/10* | (2006.01) |
| *G21H 3/02* | (2006.01) |
| *G21K 5/00* | (2006.01) |
| *H01J 65/06* | (2006.01) |
| *H01J 65/08* | (2006.01) |

(52) U.S. Cl. .................. 356/317; 356/417; 250/458.1; 250/459.1

(58) Field of Classification Search ..................... None
See application file for complete search history.

(56) References Cited

U.S. PATENT DOCUMENTS 5,243,546 A * 9/1993 Maggard .................... 702/90

(Continued)

FOREIGN PATENT DOCUMENTS

DE 42 10 970 A1 10/1993

(Continued)

OTHER PUBLICATIONS

Alexander Breunig: "Mulikomponentenanalyse im Sekndentakt", GIT Labor-Fachzeitschrift, Apr. 2000, p. 430-433.

(Continued)

*Primary Examiner*—Gregory J. Toatley, Jr.
*Assistant Examiner*—Gordon J. Stock, Jr.
(74) *Attorney, Agent, or Firm*—Akerman Senterfitt; Stephan Pendorf; Yonghong Chen

(57) ABSTRACT

A method and a device for image producing measurement of fluorescent light, according to which a sample containing fluorophores of different species is irradiated with excitation light of at least one excitation channel defined by its spectral properties. The fluorescent light emitted by the sample is received by at least one detection channel defined by its spectral detection characteristic, and is converted into a digital signal, which is stored for further processing The properties of a number of measuring channels, respectively defined as specific combinations consisting of an excitation channel and a detection channel, are automatically set before conducting the measurement according to the result of a mathematical optimization process, which takes into account the fluorescence characteristics of at least some of the fluorophores presumed by the user to be in the sampler.

19 Claims, 1 Drawing Sheet

U.S. PATENT DOCUMENTS

| | | | |
|---|---|---|---|
| 5,324,940 A * | 6/1994 | Ekstrom | 250/302 |
| 5,568,400 A * | 10/1996 | Stark et al. | 702/85 |
| 6,166,853 A * | 12/2000 | Sapia et al. | 359/559 |
| 6,200,818 B1 | 3/2001 | Eigen | |
| 6,300,639 B1 | 10/2001 | Wiederhoeft | |
| 6,384,914 B1 | 5/2002 | Drexhage | |
| 6,741,346 B1 | 5/2004 | Gerstner | |
| 6,995,840 B2 * | 2/2006 | Hagler | 356/310 |
| 2004/0022684 A1 * | 2/2004 | Heinze et al. | 422/82.08 |
| 2004/0181375 A1 * | 9/2004 | Szu et al. | 703/2 |
| 2005/0017160 A1 * | 1/2005 | Wolleschensky et al. | 250/234 |

FOREIGN PATENT DOCUMENTS

| | | |
|---|---|---|
| DE | 197 18 016 A1 | 11/1998 |
| DE | 197 57 740 A1 | 7/1999 |
| DE | 198 29 944 C2 | 1/2000 |
| DE | 199 15 137 C2 | 10/2000 |
| DE | 199 30 532 A | 1/2001 |
| DE | 199 56 620 A1 | 5/2001 |
| DE | 100 08 594 A1 | 8/2001 |
| DE | 100 35 190 A1 | 2/2002 |
| WO | WO 01 09592 A | 2/2001 |

OTHER PUBLICATIONS

Daniel L. Farkas et al.: "Non-invasive image acquisition and advanced processing in optical bioimaging", Computerized Medical Imaging and Graphics, 22 (1998), p. 89-102.

M.E. Dickinson et al.: "Multi-Spectral Imaging and Linear Unmixing Add a Whole New Dimension to Laser Scanning Fluorescence Microscopy", BioTechniques 31, Nr. 6 (2001), p. 1272-1278.

Joe W. Boardman: "Inversion of imaging spectrometry data using singular value decomposition"; Proc. IGARSS, 89, Nr. 4 (1989), p. 2069-2072.

* cited by examiner

METHOD AND DEVICE FOR CONDUCTING THE SPECTRAL DIFFERENTIATING, IMAGING MEASUREMENT OF FLUORESCENT LIGHT

CROSS REFERENCE TO RELATED APPLICATION

This application is a national stage of PCT/EP03/05094 filed 15 May 2003 and based upon DE 102 22 359.9 filed 21 May 2002 under the International Convention.

FIELD OF THE INVENTION

The invention refers to a method for spectrally differentiating imaging measurement of fluorescent light Furthermore, the invention refers to a device for spectrally differentiating imaging measurement of fluorescent light.

BACKGROUND OF THE INVENTION

Such methods and devices find application especially in modern biology today. Especially for fluorescence microscopy, a number of specific fluorescence probes have been developed. These are suitable, for example, for specific labeling of antibodies, certain DNA sequences or other biological structures. Furthermore, they include fusion constructs of certain proteins with fluorescent proteins, such as GFP (Green Fluorescent Protein) or YFP (Yellow Fluorescent Protein), etc. Furthermore, special indicator dyes are included, the fluorescence of which is correlated with the concentration of certain ions, for example calcium, with respect to their intensity and/or emission spectrum.

Modern biology attempts to adjust the complexity of the measurement methods to the complexity of the investigated samples and thus many times it is interested in localizing as large a number of different markings in a sample as possible and to resolve these spatially from one another.

Another especially current problem is the quantitative determination of fluorophores which enter into interaction with one another through fluorescenceless [sic] energy transfer FRET (Fluorescence Resonance Energy Transfer). Such FRET-pairs consisting of donor and acceptor cannot be resolved from one another in an optical microscope. Rather, the superimposition of the donor and acceptor spectra or their relationship to one another is measured.

Another current problem is the separation of the fluorescence of an indicator dye into the portions of the bound and free form of the fluorophore for the purposes of obtaining the ratio and subsequent calculation of the activity of a ligand.

Another problem which occurs in almost all imaging fluorescence methods in biology is the consideration of the so-called autofluorescence, that is, the nonspecific background fluorescence which many structure exhibit, such as cells and substrate carriers.

In principle, an essential limitation of this method lies in the fact that the organic fluorophores that are usually used have relatively broad excitation and emission spectra which is attributed to the large number of phononic sublevels that participate in these organic molecules. Thus it becomes comparatively difficult to excite species of fluorophores contained in a sample in a specific way or to detect them specifically. Rather, usually one obtains a complex composition of the contributions of different species as signal.

Conventionally, the method employed is to use excitation channels which are as far away from each other as possible, and to employ as narrow detection channels as possible. The concept of excitation channel in this connection is understood to mean the sum of the properties of the light that excites the fluorescence. This includes especially the spectral properties which also includes in the framework of this description the intensity of the particular spectral components. In any case, other properties, such as the time of excitation and/or the duration of excitation combined as excitation time, can be used for the definition of an excitation channel. Analogously, here the concept of detection channel is defined as the sum of the properties of the elements which guide the fluorescent light emitted by the sample and filter and detect them. This includes again the spectral properties including the particular sensitivities toward the individual spectral components, and on the other hand the detection time, the detection time point and detection duration. Special combinations of excitation channels and detection channels are described below in a summarizing way as measurement channels.

In current practice, various methods are known which are aimed at optimum spectral resolution of the different types of fluorophores in the presence of one another and depend on the properties of the fluorophores and on their combination. Thus, for example, it is possible to carry out several recordings in succession with different excitation wavelengths in a given detection channel, where the excitation wavelengths are always chosen so that the absorption maximum of a fluorophore species is included as accurately as possible. In this case, one measurement channel is used per measurement. Another possibility consists in exciting the sample at an excitation wavelength which lies in the region of the excitation spectra of several fluorophore species and to divide the emitted light using filter sets or by cascades of beam splitters into spectral regions and then introduce these parts to separate photosensors. Thus, in this method, several measuring channels are used simultaneously. If the emission or excitation bands of the fluorophores of interest are sufficiently widely separated from one another, the frequency regions of the individual measurement channels can be chosen so that each channel corresponds to a fluorophore.

The disadvantage of these techniques is that mostly a certain cross-talk between the channels is unavoidable. This applies especially when a number of different fluorophores are used in a sample where the spectra overlap due to the limited bandwidth of usable wavelengths. Although this can be counteracted by sharply limiting the spectral limits of the individual detection channels, for example, by using narrow band pass filters, the consequence is that a large number of the fluorescence photons do not contribute to the signal, which has an adverse effect on the quality of the detected signal. This is especially undesirable because, due to bleaching processes of the fluorophores in the sample, the total number of photons that can be emitted by a given preparation is limited, but also because, due to photon noise, the quality and resolution of a measurement becomes better when more photons contribute to the measurement. Although almost all fluorescence photons can be made useful by breaking up the emitted fluorescent light spectrally and then treating the spectrum with the aid of a large number of spectral channels, the relative noise increases considerably in each individual extremely narrow channel, because only comparatively few photons are available for each individual channel, so that this method is only suitable in cases of application where the light intensity is especially high.

The problems addressed above can be reduced greatly when broad measurement channels are used, the cross-talk of which is deliberately taken into account and the received data are subjected to a considerable mathematical processing or evaluation. For this purpose, the received signals are converted in the detectors or in connected conversion units into digital data, and then these are stored in a memory unit of a digital data processing equipment. In many cases, for example in laser scanning microscopy (LSM), digitalization and subsequent processing of the data is an essential component of the technique.

The evaluation of the data mentioned above is usually done with the aid of a computer unit of the digital data processing equipment. Especially good results were obtained with the so-called "linear unmixing" method. This method is based on setting up and solving an inhomogeneous linear system of equations which, using the known properties of the measurement channels, establishes a relationship between the measured signal and the fluorophore composition in the sample. This system of equations can be represented mathematically in a matrix representation as $$\vec{y} = A\vec{B} + \vec{I} \cdot \vec{b} \quad (1)$$

or in a component representation $$y_r = \sum_{\mu=1}^{p} I_r a_{\mu r} B_\mu + I_r b_r \quad (2)$$

These formulas are to be understood as follows: The vector $\vec{B}$ represents the different species of fluorophores in their relative concentration at a given image point. Let p be the number of different fluorophore species. Thus, the vector $\vec{B}$ has p components $B_\mu$. The vector $\vec{y}$ represents the signal detected in each measurement channel. Let q be the number of measurement channels. Thus, the vector $\vec{y}$ has q $y_r$ components. For example, if four different excitation wavelengths and four different spectral detection windows were used, the number of measurement channels is q=16. The vector $\vec{I}$ represents the excitation intensity used for each measurement channel and thus has q components $I_r$. The matrix A is the coefficient matrix which links the chemical composition $\vec{B}$ of the fluorophores through the excitation intensities $I_r$ of the excitation channels and the other properties $a_{\mu r}$ of the measurement channels to the resulting signal $\vec{y}$. Thus, the matrix A has pq elements $I_r a_{\mu r}$. Finally, the vector $\vec{b}$ with q components $b_r$ is a correction quantity which represents the scattered light or another background light in each measurement channel. The quantities $B_\mu$ are usually to be regarded as location dependent, while the other quantities on the right side of equations (1) and (2) represent parameters which are normally the same for all pixels. Autofluorescence of the measured object can be treated either as fluorescence of an additional fluorophore $B_\mu$ or as background light $b_r$ (in case it is location independent). In the case of FRET, an FRET-pair can be considered as an independent chromophore, the concentration of which is given through one of the quantities $B_\mu$.

The goal of "linear unmixing" is to find the solution B of the above linear system of equations, which is possible mathematically by simple inversion of the coefficient matrix A as long as the number of equations q is greater than or equal to the number of different fluorophore species p. For the algorithmic conversion of this mathematical operation, a number of numerical methods are known to the person skilled in the art. An explanation of this technique is given in *Farkas et al.: "Non-invasive image acquisition and advanced processing in optical bio-imaging", Computerized Medical Imaging and Graphics,* 22 (1998), p. 89-102 or *Dickinson et al.: "Multi-spectral imaging and linear unmixing at whole new dimension to laser scanning fluorescent microscopy", BioTechnics,* 31, No. 6 (2001), p. 1272-1278 as well as *Boardman: "Inversion of imaging spectroscopy data using singular value decomposition", Proc. IGARSS,* 89, No. 4 (1989), p. 2069-2072. An implementation of this method of evaluation in LSM device was realized by the company Carl Ziess, Jena, Germany, in their Laser-Scanning-Microscope LSM 510 meta.

As explained, the method of linear unmixing represents a proven means of data evaluation when knowing the properties of the measurement channels used. However, a disadvantage is that the selection of suitable measurement channels, that is, the adjustment of all parameters, such as excitation wavelength, excitation intensity, excitation time and detection wavelength and detection time is left to the intuition of the user, as before. However, since intuition is guided by concrete rules which are obvious to the user, as before, if possible, a fluorophore species should be assigned to each measurement channel so that the possibilities provided by complex data analysis are usually not utilized.

SUMMARY OF THE INVENTION

The task of the present invention is to provide a generic process with which the quality of the obtained data is improved in a simple way.

Another task of the present invention is to further develop the generic device in such a way that the results obtained with it can be improved in a simple manner.

These tasks are solved by a method and by a device with the characteristics of the independent claims.

Further embodiments of the present invention are given in the dependent claims.

The invention is based on a generic method by the fact that the properties of several measurement channels are adjusted automatically before carrying out the measurement, or the user is given the corresponding instructions for manual adjustment. The automatic adjustments or the instructions are based according to the results of a mathematical optimization method carried out by a computer unit of the digital data processing equipment. In this, the fluorescence characteristic of at least some of the fluorophores contained in the sample are taken into consideration. Such a mathematical optimization method is strictly distinct from the automatic control of certain standard adjustments which can be programmed from the manufacturing plant or can be oriented by a setting library installed by the user himself. Rather, the user of the data processing equipment enters the fluorophores that he presumes to be present in the sample and their characteristics. These data are then used as the basis of the mathematical optimization method which calculates the optimized settings of the measurement channels for the special needs of the user. Thus, especially contrasting to intuition, but based on a mathematical evaluation of obtained data, a very favorable segmentation of the entire fluorescence spectrum can be performed, instead of cutting out narrow bands with filters and reducing the number of photons contributing to the signal and reducing the signal quality unnecessarily.

Advantageously, the characteristics of a number of fluorophores are stored in one or several libraries in a memory unit of the digital data processing equipment so that when the user identifies the fluorophores presumed to be present in the samples, this is sufficient without having to enter all their complete characteristics.

It is especially favorable when, within the framework of the mathematical optimization method, a linear system of equations is set up which describes the relationship between the chemical composition of the sample presumed by the user and the signal resulting based on the properties of the measurement channels to be optimized. This characteristic is based on the mathematical foundation of "linear unmixing". In any case, this basic idea operates exactly opposite to the state of the art. Namely, while in the case of "linear unmixing" in the case of known components $Y_r$ and known coefficients $a_{\mu r}$ that describe the measurement channel and the relative concentrations $B_\mu$ of the individual fluorophore species are searched for, the aim of the method according to the invention is rather to vary the coefficients $a_{\mu r}$ describing the measurement channels and thereby to carry out an optimization of the system in the sense that the solution of the system of equations can be done as uniquely as possible. The optimization is directed towards the fact that the system of equations can be solved, especially that they are unique. In this way, it can be ensured that the evaluation method which follows the measurement, which is based on the method of "linear unmixing", does not fail due to the fact that the coefficients which describe the measurement channel were chosen in the special case so that the number of linear independent equations of the system is lower than the number of existing fluorophore species, and thus the system of equations can no longer be solved uniquely.

However, advantageously, the optimization method is designed to be so flexible that it is not optimized exclusively with regard to the solvability or uniqueness of the solution of the system of equations, but additionally other conditions selected by the user are also taken into consideration. Examples of such other considerations will be explained in more detail below.

Advantageously, the optimization method includes the optimization of a condition number of a matrix expression which contains the matrix formed from the coefficients of the above-mentioned linear system of equations. Within the framework of the present invention, this is to be understood so that the algorithmic implementation of the method according to the invention can be represented mathematically as optimization of a condition number of the said matrix expression. Depending on the concrete conversion, it can be possible to omit explicit definition of a matrix or of an array within the framework of a computer program.

In an especially preferred manner, the matrix expression on which the calculation of the condition number is based is formed as matrix product on the left side of the matrix A with its transpose $A^T$, that is $A^T A$. This is based on the consideration that the expressions of equation (1) and (2) can be converted by multiplication on the left side by $A^T$ to obtain $$A^T(\vec{y} - \vec{I} \cdot \vec{b}) = A^T A \vec{B} \quad (3)$$

As it is well-known, multiplication on the left with the transposed matrix makes the obtained matrix expressions symmetric, which corresponds to a calculation of most probable values in the sense of the Gaussian minimization of the residual sum of squares.

In case of explicit consideration of the noise of the measurement channels, a matrix weighted by the measurement errors expected by the user can be employed, which can be regarded as minimization of the quantity $\chi^2$ (chi square) known from statistics.

Thus, for example, in a preferred embodiment, the condition number to be optimized corresponds essentially to the determinant of the matrix expression, especially of the expression $A^T A$. Alternatively, condition numbers which also contain the trace N of the matrix expression can also be used as optimization criterion. In a further practical example of the method according to the invention, the quantity $$\det / \left(\frac{N}{n-1}\right)^{n-1/2} \quad (4)$$

is used as the condition number to be optimized, where det is the determinant, N the trace and n the dimension of the matrix expression. In another advantageous practical example of the method according to the invention, the ratio of the smallest to the largest eigenvalue of the matrix expression is used as condition number. It was shown that the optimization of each of these condition numbers leads to a selection of measurement channel properties by variation of the matrix elements $I_r a_{\mu r}$, which, although oppose intuition in many cases, provide outstanding results with regard to the data evaluation performed after the measurement, especially using the method of "linear unmixing".

Here, the optimization of different condition numbers leads to results of different quality in different constellations of cases. It is therefore especially advantageous to further develop the method according to the invention so that the user is given the possibility to give a global characteristics of the expected measurement result, for example, very weak fluorescence, especially large number of different fluorophores which are especially close spectrally, etc., and thus to establish or to directly establish the condition number to be optimized.

The conversion of the calculated optimization result into the realization of physical properties of the measurement channels can be carried out in many ways. Thus, for example, a selection of a frequency or frequency band in the excitation and/or detection beam path can be used through adjustable filters, such as AOTFs (Acousto-Optic Tunable Filters) or LCTFs (Liquid Crystal Tunable Filters). Similarly, fixed cut-off filters, band-pass filters and/or beam splitters, which are arranged, for example, on motor-driven filter sleds or filter wheels can be used. Another possibility of automatically influencing the measurement channel characteristics consists in the variation of the excitation intensities, for example, by the introduction of the so-called wedge filters in the excitation beam path. The time characteristics of the measurement channels can be varied in the conversion of the optimization method according to the invention. For example, the duration of excitation can be varied or time detection windows can be defined for separation of fluorescent components with shorter and longer life. A number of conversion possibilities are known to the person skilled in the art in this regard.

Condition numbers of matrices as mentioned above essentially provide estimates of maximum errors, but in practice these can be much smaller. This applies especially when known structures of a given problem are taken into consideration. In an especially advantageous further development of the method of the invention, therefore the possibility of far-reaching optimization is provided in which the special properties of the experimental sources of perturbations are formulated for fluorescence measurements. Especially advantageously, a second optimization step is provided in which the noise of the expected signal is optimized by variation of the coefficients that describe the properties of the measurement channels.

This inventive idea is based on the following recognition. If the coefficients of matrix A or of the matrix expression $A^T A$ are determined, preferably optimized by using the first optimization step described above, the solution of the linear system of equations is as follows:

$$<\vec{B}> = (A^T A)^{-1} A^T (\vec{y} - \vec{I} \cdot \vec{b}) \qquad (5)$$

Here $<\vec{B}>$ shows the expectation value of the solution $\vec{B}$ in which it is taken into consideration that the vector $\vec{y} - \vec{I} \cdot \vec{b}$ has an experimental variation $\vec{\sigma}$. The vector $\vec{\sigma}$ is to be understood as component-wise square root of the expression $\sigma_r^2$, which are always to be understood as the expectation values of the variance of the measured value $y_r$. These were composed of two components, namely the photon noise, the variance of which is proportional to the signal level, and the constant detector noise, which is statistically independent of it, and is composed of dark current and the selection noise [read-out noise] of the particular detector.

$$\sigma_r^2 = y_r s + \sigma_{0,r}^2 \qquad (6)$$

Here s is a proportionality constant (a suitably calculated individual photon contribution) and $\sigma_{0,r}^2$ is the sum of all constant contributions to the variance of the signal in channel r.

According to the method of the Gaussian error propagation, the variation $\sigma_{\mu B}$ of component $B_\mu$ of the vector $\vec{B}$ can described by $$\sigma_{B\mu}^2 = \sum_{r=1}^{q} \left[ \frac{\partial \langle B_\mu \rangle}{\partial y_r} \right]^2 \sigma_r^2 \qquad (7)$$

Since equation (5) is a linear system of equations and $\vec{I} \cdot \vec{b}$ does not depend on $y_r$, we have $$\frac{\partial \langle B_\mu \rangle}{\partial y_r} = c_{\mu r},$$

where $c_{\mu r}$ is the element of the r-th line of the μ-th column of the matrix $C = (A^T A)^{-1} A^T$. Therefore, we have $$\sigma_{B\mu}^2 = \sum_{r=1}^{q} c_{\mu r} \sigma_r^2 \qquad (8)$$

This expression or also the sum of all squared deviations $$S_B^2 = \sum_{\mu=1}^{p} \sum_{r=1}^{q} c_{\mu r} \sigma_r^2 \qquad (9)$$

can be minimized in the space of all measurement channel parameters. In any case, according to equation (6), the quantities $\sigma_r^2$ contain the measured values $y_r$, so that for the minimization of $S_B^2$, the user has to provide information about the size of the expected signals.

In an especially advantageous embodiment of the method according to the invention, it is essentially this quantity $S_B^2$ which is optimized by variation of the coefficients describing the measurement channels.

Hereby, it is preferably provided that the noise of the signal to be expected is optimized with consideration of one or more of additional conditions that can be introduced by the user. One of these additional conditions, which can also be used within the framework of the first optimization step described above, in an advantageous embodiment of the method according to the invention, could be a maximum limit for the bleaching of one or several fluorophores. Since as bleaching progresses, the signal will decrease, while certain components of the noise are independent of time, under certain circumstances the optimization can be performed with reference to the duration of illumination or its intensity. As another possible additional condition, the minimization of the noise of a signal of a certain intensity, preferably predetermined by the user, can be utilized with advantage. This additional condition is especially useful when the expected signal is so low that the total noise of the measurement channel is dominated by the dark current and by the read-out noise of the detector.

As another possible additional condition, in an advantageous embodiment of the method according to the invention, the maximum spectral resolution of the different fluorophores in a given region of a previously recorded test image can be utilized. This becomes especially significant where one or several different fluorophores are to be resolved with the background of a general non-specific autofluorescence of the sample or in case a certain image region is of special interest to the user.

In another favorable embodiment of the method according to the invention, it is provided that the minimization of the relative error of the measurement channels be used as an additional condition. This form of additional condition is preferably introduced when ratio measurement such as in FRET measurements are to be performed.

It can be especially favorable when the user has the possibility to enter, in addition to one or several additional conditions, or, instead of that, to enter information to a presumed model of the noise, for example, based on poison.

In an especially preferred manner, the optimization method according to the invention is carried out within the framework of an iterative, dialog-controlled process for the definition of additional conditions, which permits the user to enter additional information after performing a preliminary optimization step and to add one or several additional optimization steps.

In order to be able to utilize the advantages and special characteristics of the method according to the invention in an especially advantageous manner, according to the invention a device is made available, for example, a laser scanning microscope, the digital data processing equipment of which is programmed in such a way that the previously described optimization process according to the invention can be performed and which has the above-mentioned technical devices for automatic adjustment of the measurement channel properties.

BRIEF DESCRIPTION OF THE DRAWING

A preferred embodiment of the method according to the invention and of the system according to the invention will be described below with the aid of the attached drawing. The only drawing is FIG. 1 which shows the schematic structure of a laser scanning microscope equipped according to the invention.

DETAILED DESCRIPTION OF THE DRAWINGS

Figure 1:
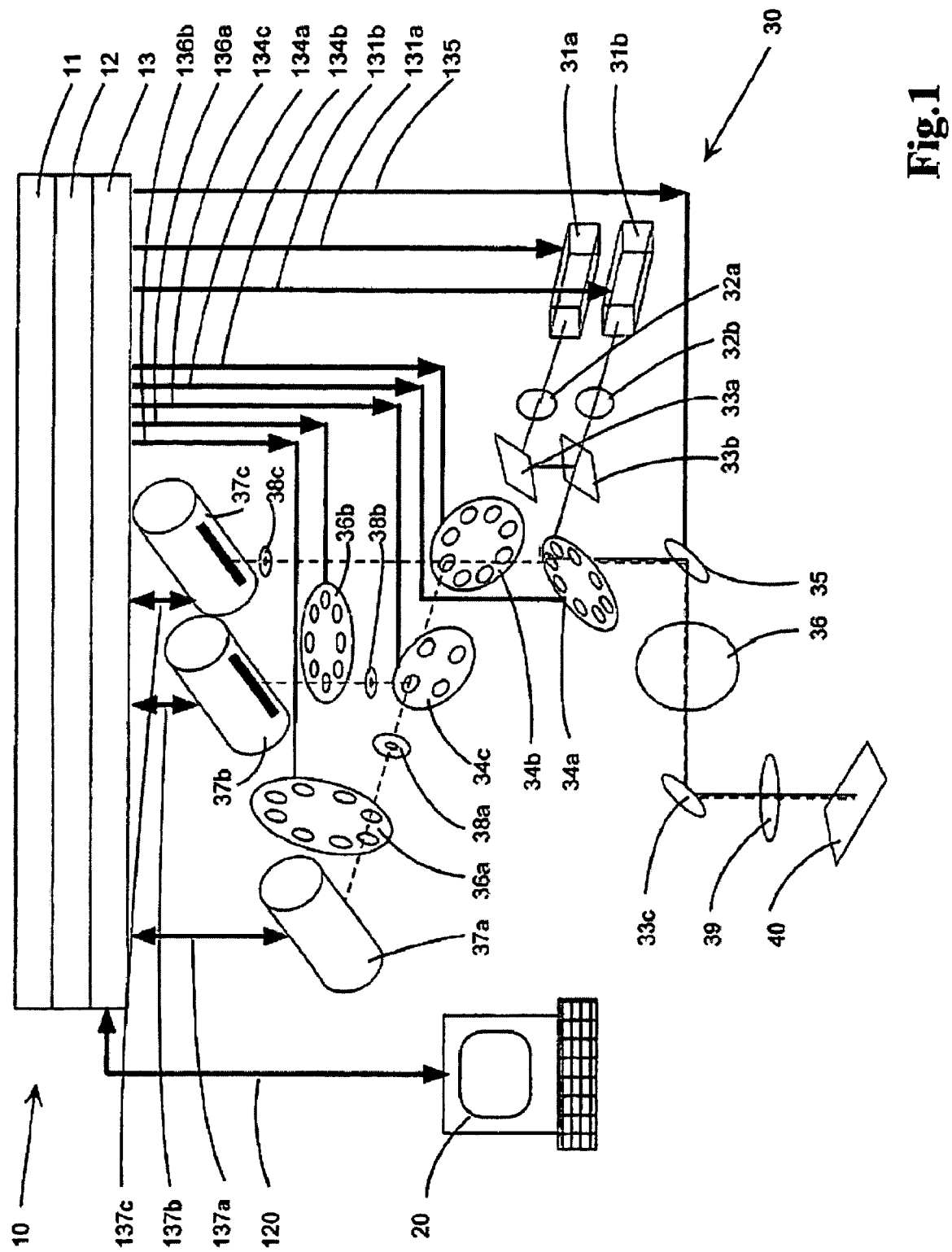

The especially advantageous practical example of the device according to the invention shown in FIG. 1 is realized as a laser scanning microscope. The system consists essentially of three parts, namely a data processing installation 10, a user-interface 20 as well as an optical/electronic structure 30. The data processing installation includes a computer unit 11 in which the optimization method according to the invention as well as preferably the calculations necessary for the evaluation of the recorded data are performed. Furthermore, a memory unit 12 is included in which the recorded data are stored or can be buffered but also in which the program commands as well as libraries necessary for carrying out the method according to the invention are stored. The library contains the data necessary for the calculations according to the invention. These are excitation spectra, fluorescence spectra as well as fluorescence lifetimes, number of fluorophores, spectral characteristics of number of filters or color splitters, as well as the sensitivity characteristics of different detectors. The spectral and electronic characteristics of different light sources, especially lasers, can be stored in the memory unit 12 of the data processing installation 10.

Furthermore, the data processing installation 10 has a data interface 13 through which the recorded data as well as user inputs are fed through the user interface 20 into the data processing installation 10 and control commands to adjustable components of the optical/electronic structure 30 of the device as well as information to the user interface 20 can be outputted.

The above elements of the data processing installation 10 can be realized in many ways known to the person skilled in the art and the technical details can be adapted to the special particular configuration.

In order to measure a fluorescent sample 40, it is placed under the microscope objective. Through the user interface 20, the user can enter various data into the data processing installation 10, such as the presumed chemical fluorophore composition, expected intensities and/or optimization conditions, for example bleaching limits. Based on these data, the computing unit 11 of the data processing installation 10 calculates according to the optimization method of the invention the values according to which the optical/electronic structure 30 has to be set. As a result of this the measurement channels are defined as specific combinations of special excitation and detection channels. In the practical example shown in FIG. 1, the excitation channels are designed comparatively simply. They consist essentially of two laser sources 31a and 31b which illuminate the sample 40 through the microscope objective 39 through motor-controllable collimators 32a, 32b, deviation mirrors 33a, 33b, 33c, a motor-controllable beam splitter 34a, a scanning mirror 35 and a scanning lens 36. The properties of the excitation light with respect to wavelength and intensity can be adjusted by controlling laser 31a, 31b, collimators 32a, 32b, as well as the beam splitter wheel 34a through control lines 131a, 131b and 134a. Naturally, it is within the realm of the invention to use light sources of other types and/or other numbers, or to adjust the properties of the excitation light with other or additional controllable components, such as neutral gray filter slides.

The control of the scanning mirror 35 through control line 135 is done in the conventional manner.

The fluorescent light, which is shown in FIG. 1 schematically as a dashed line, goes from sample 40 through the microscope objective 39, deviation mirror 33c, scanning lens 36 and scanning mirror 35 to the motor-controllable beam splitter wheel 34a. With suitable adjustment of wheel 34a, the essential part of the fluorescent light goes through the adjusted beam splitter, while light in the region of the excitation wavelengths is reflected. The setting of the detection channels is done by adjusting this beam splitter wheel 34a as well as by adjusting other beam splitter wheels 34b and 34c, which are adjusted through the control lines 134b and 134c according to the parameters determined by the optimization method according to the invention. Another channel specification is done through the setting of the filter wheels 36a and 36b, which are adjusted through control lines 136a and 136b according to the parameters determined by the optimization method according to the invention.

The fluorescent light thus preselected falls on various detectors 37a, 37b and 37c, the data of which are fed through the input lines 137a, 137b and 137c into the data processing installation 10. Depending on the special construction, the data are digitized already in detectors 37a, 37b, 37c, or only in the data interface 13 of the data processing installation 10. The data thus recorded and stored in the memory unit 12 of the digital processing installation 10 are evaluated by the computer unit 11 using known data evaluation programs, where preferably the method of "linear unmixing" finds application.

The adjustment or definition of the measurement channels according to the invention refers to the practical example, to the spectral sectioning of the fluorescent light as well as to the number of measurement channels used, that is, the number of combinations of excitation and detection channels used. Here the number and nature of the detectors is as variable as the light sources are. Especially, not shown in FIG. 1, detectors can be used which can be controlled regarding their detection time, that is, detection duration and/or detection time point according to calculated optimization parameters. Naturally, it is also possible to create the pinholes 38a-c necessary for the LSM structure and to include their diameter in the series of optimization parameters.

Naturally, the embodiment described and shown in FIG. 1 of a device according to the invention is only an illustration of an example of an especially advantageous variant. However, many variations can be conceived within the realm of the present invention.

| Reference Number List | |
|---|---|
| 10 | Digital data processing installation |
| 11 | Computing unit of 10 |
| 12 | Memory unit of 10 |
| 13 | Data interface of 10 |
| 120 | Control lines |
| 131a,b | Control lines |
| 134a-c | Control lines |
| 135 | Control lines |
| 136a,b | Control lines |
| 137a-c | Control lines |

-continued

Reference Number List

| 20 | User interface |
| 30 | Optical/electronic structure |
| 31a,b | Laser |
| 32a,b | Collimator |
| 33a-c | Deviation mirror |
| 34a-c | Beam splitter wheel |
| 35 | Scanning mirror |
| 36 | Scanning lens |
| 37a-c | Detector |
| 38a-c | Pinhole |
| 39 | Microscope objective |
| 40 | Fluorescent sample |

We claim:

1. A method for an image producing measurement of fluorescent light, comprising:
   irradiating a sample, containing fluorophores of at least one species, with exciting light of at least one excitation channel defined by its spectral properties, and
   receiving the fluorescent light emitted by the sample by at least one detection channel defined by its spectral detection characteristic and converting it into a digital signal,
   storing the digital signal in a memory unit of a digital data processing unit, and
   producing an image or image file of the sample based on the digital signal,
   wherein, prior to carrying out a measurement, properties of the at least one excitation channel and the at least one detection channel are predetermined according to a result of a mathematical optimization process carried out by a computing unit of the digital data processing unit, which takes into consideration fluorescence characteristics of at least one of the fluorophores presumed by a user to be in the sample, wherein
   the optimization process includes
   a) setting up a linear system of equations,
      coefficients of which represent spectral characteristics of measurement channels, which are respectively defined as a combination of one excitation channel and one detection channel, and
      which describes a relationship between a user-presumed chemical composition of the sample and a signal calculated based on the measurement channel characteristics to be optimized,
   b) varying the coefficients, until a unique solution to the equation system becomes possible,
   c) the coefficients calculated as a result of the optimization process forming a basis of the predetermination of the properties of the excitation and detection channels.

2. The method according to claim 1, wherein the uniqueness of the solution of the linear system of equations is optimized taking into consideration one or more additional conditions that can be introduced by the user.

3. The method according claim 1, wherein the mathematical optimization method includes the optimization of a condition number of a matrix expression containing a matrix formed from the coefficients of the linear system of equations.

4. The method according to claim 1, wherein the mathematical optimization method contains a second optimization step in which a noise of an expected signal is optimized by variation of coefficients which describe properties of the measurement channels.

5. The method according to claim 2, wherein a maximum limit or an optimum for the bleaching of one or several fluorophores is used as additional condition.

6. The method according to claim 2, wherein a minimization of the noise of a signal of a given intensity is used as additional condition.

7. The method according to claim 2, wherein a maximum spectral resolution of different fluorophores in a region of a previously recorded test image is used as additional condition.

8. The method according to claim 2, wherein a minimization of a relative error is used as additional condition.

9. The method according to claim 2, wherein the optimization method includes an iterative, dialog-controlled process for a definition of the additional conditions.

10. The method according to claim 2, wherein an automatic adjustment of measurement channel properties is carried out by starting and/or motor motion of AOTFs, LCTFs, cut-off filters, band pass filters or neutral gray filters and/or beam splitters.

11. The method according to claim 3, wherein matrix elements of the matrix expression are weighted for minimization of a quantity $\chi^2$ corresponding to measurement errors expected by the user.

12. The method according to claim 3, wherein the matrix expression containing the coefficient matrix is essentially a left-side matrix product of the coefficient matrix with its transposed form.

13. The method according to claim 3, wherein the condition number contains essentially the determinant of the matrix expression.

14. The method according to claim 3, wherein the condition number contains essentially the trace of the matrix expression.

15. The method according to claim 3, wherein the condition number corresponds essentially to a quantity $$\det / \left(\frac{N}{n-1}\right)^{(n-1)/2},$$

where det is the determinant, N is the trace and n is the dimension of the matrix expression.

16. The method according to claim 3, wherein the condition number contains essentially a ratio of the smallest to the largest intrinsic value of the matrix expression.

17. The method according to claim 3, wherein the condition number to be optimized can be chosen by the user.

18. The method according to claim 17, wherein the condition number to be optimized is chosen by the user by entering a global characterization of a signal to be expected into the digital data processing unit and then the condition number is determined automatically.

19. The method according to claim 4, wherein the noise of the signal to be expected is optimized taking into consideration one or more additional conditions that can be introduced by the user.

* * * * *